United States Patent [19]
Moore

[11] Patent Number: 5,447,688
[45] Date of Patent: * Sep. 5, 1995

[54] DETECTOR, AND METHOD OF USING SAME

[76] Inventor: Robert E. Moore, 2865 Danbe Rd., Oshkosh, Wis. 54904

[ * ] Notice: The portion of the term of this patent subsequent to Jul. 26, 2011 has been disclaimed.

[21] Appl. No.: 122,391

[22] Filed: Sep. 16, 1993

Related U.S. Application Data

[63] Continuation-in-part of Ser. No. 814,720, Dec. 30, 1991, Pat. No. 5,332,548.

[51] Int. Cl.$^6$ .............................................. G01N 31/22
[52] U.S. Cl. ........................................ 422/56; 422/61; 422/87; 436/3; 436/130; 436/169
[58] Field of Search ................. 422/56–58, 422/61, 86, 87; 436/3, 130, 167, 169, 181

[56] References Cited

U.S. PATENT DOCUMENTS

| | | | |
|---|---|---|---|
| 3,830,094 | 8/1974 | Leger | 73/15.4 |
| 3,945,798 | 3/1976 | Young | 23/230 R |
| 4,380,587 | 4/1983 | Koocher | 436/128 |
| 4,597,942 | 7/1986 | Meathrel | 422/87 |
| 5,096,813 | 3/1992 | Krumhar et al. | 435/28 |
| 5,096,836 | 3/1992 | Macho et al. | 422/56 |
| 5,166,051 | 11/1992 | Killeen et al. | 422/56 |
| 5,171,536 | 12/1992 | Evers | 422/86 |
| 5,179,002 | 1/1993 | Fehder | 422/87 |
| 5,332,548 | 7/1994 | Moore | 422/56 |

*Primary Examiner*—Donald E. Czaja
*Assistant Examiner*—Milton I. Cano
*Attorney, Agent, or Firm*—R. Jonathan Peters

[57] ABSTRACT

A detector, which is source specific, for detecting a fugitive emission from a component containing a gaseous or volatile analyte, and is adaptable for adjacent disposition to the component. The device includes (a) a substrate for disposition adjacent the component from or through which the analyte is emitted, said substrate being substantially inert to the analyte, (b) an analyte-reactive reagent, and optionally (c) an indicator. The substrate is isolated from the ambient air or atmosphere, and no exogenous reagent is utilized by the detector or in the process of detection. When the detector is applied adjacent the component, a detectable reaction occurs (e.g., color-forming reaction or signal) with the analyte emitted.

33 Claims, 7 Drawing Sheets

DETECTOR, AND METHOD OF USING SAME

This application is a continuation-in-part application of application U.S. Ser. No. 07/814,720 filed on Dec. 30, 1991, now U.S. Pat. No. 5,323,548.

FIELD OF THE INVENTION

This invention relates to a detector for detecting a fugitive emission from a component, and to the method of using the detector. In its more specific aspect, this invention relates to a source specific detector for detecting a fugitive emission from a component containing a gaseous or volatile analyte, and to the method of using the detector.

BACKGROUND OF THE INVENTION AND PRIOR ART

In a large number of processing industries, gaseous or volatile materials, especially volatile organic compounds, are transported along or through a system or network having incorporated therein varied components including, for example, pipe lines, valves, fittings (including flanges, seals, and threaded connections), pumps, compressors, pressure relief devices, diaphragms, hatches, sight-glasses, meters, and the like. These industries include most notably the hydrocarbon processing industries such as petroleum refineries, chemical and petrochemical plants, oil and gas production gas facilities, natural gas processing facilities, and pipeline transfer stations, but might also include other industries or facilities such as the pharmaceutical industry, wood products industry, the ceramic industry, and the like. Any of these components interconnected throughout the plant or facility are susceptible to leaks especially at a joint or juncture due to such factors as defects in the equipment or in the connecting parts, temperature variations causing an expansion and contraction of the component especially at a joint, corrosion, or mishandling by a worker. Many or most of these gaseous or volatile organic compounds utilized or produced in these industries can be potentially toxic or hazardous, and therefore it is essential to maintain a tight system so as to avoid or minimize any leaks. For example, in order to provide a tight connection at a joint or juncture, three classes of joints are in conventional use: viz., welded joints, flanged joints, and a stuffing box as at meter and valve joints. A leak at a juncture can develop at anytime with all three classes, but the latter two are more probable to be troublesome.

The organic compounds produced or used by industry fulfill a need, and therefore usage is expansive and commonplace, and include, for example, aliphatic and aromatic hydrocarbons, alcohols, aldehydes, ketones, esters, amines, etc., and are used in or for fuels, plastics, resins, adhesives, paints, coatings, solvents, pharmaceuticals, foods, etc. However, many such organic compounds are volatile and emit antigenic or noxious fumes or gases as well as hazardous fumes or gases that can cause a fire or explosion. Moreover, the plant may generate or utilize other fumes or gases such as hydrogen or ammonia, which are noxious or hazardous. Numerous precautions or safety standards have been implemented by industry to detect or identify the sources of the gaseous or volatile fumes, to control the exposure of the worker or the environment to these fumes or gases, and to prevent the ingestion or inhalation of these fumes or gases by the worker or others within the area. Many of these fumes or gases have known toxic characteristics, and can cause irritation to the skin, eyes, nose or throat, or cause headaches, drowsiness or digestive disorders, are pathological or cause damage to internal organs (e.g., liver) or can be carcinogenic. The problem may be latent, and this noxious effect can be long-term and persist several years after the exposure to the gaseous fumes.

Several detectors or analytical devices have been developed for the purpose of detecting and monitoring gaseous or volatile emissions. Such known devices typically involve electronic instrumentation such as spectroscopy, and/or use x-ray detection, gas chromatography, laser detection, mass spectrometry, or ultrasonics, and further require comparisons and calibrations against standards and controls. In another type of detector, the analyte is drawn, sucked or pump across or over a reagent reactive with the gaseous analyte, but these detectors are not isolated from the ambient air and, therefore, are not applicable or useful for detecting in situ a fugitive emission. Techniques utilizing these devices are labor intensive and require constant, usually daily, visual and audible checking by a worker who is required to observe or test each individual joint. Also, soaps, detergents, and solutions have been used to check for leaks, and dyes have been used at joints to detect for leaks, but these are of questionable reliability, but tend to be highly variable and unreliable.

This invention has, therefore, as its purpose to provide a detector which is source specific, and to the method of using same, for detecting in situ a fugitive emission from a component containing a gaseous or volatile analyte; further requires minimal or no technical training, instrumentation, operator time, or special analyses; and is convenient, transportable, rugged, and inexpensive.

SUMMARY OF THE INVENTION

Broadly, this invention provides a detector, which is source specific, for detecting a fugitive emission from a component containing a gaseous or volatile analyte, and is adaptable for adjacent disposition to the component. The device comprises (a) a substrate for disposition adjacent the component from or through which the analyte is emitted, said substrate being substantially inert to the analyte, (b) an analyte-reactive reagent, and optionally (c) an indicator. The substrate is isolated from the ambient air or atmosphere, and no exogenous reagent is utilized by the detector or in the process of detection. When the detector is applied adjacent the component, a detectable reaction occurs (e.g., color-forming reaction or signal) with the analyte emitted. In accordance with one embodiment of the invention, the detector is autogenous in that the analyte-reactive reagent provides the color signal, but this will depend on such factors as the reagent selected and the analyte in question. In an alternative embodiment, an indicator is used in conjunction with the analyte-reactive reagent. Because the detector is adjacent the component, and is isolated from the ambient air or atmosphere, the fugitive emission in question reacts with the analyte-reactive reagent thereby detecting or indicating a leak from the component, per se, which is in contrast to detecting a volatile or gaseous analyte in ambient or atmospheric air that could have originated from another source. Moreover, it is not necessary to draw, suck or pump the analyte along with ambient air across or over the analyte-reactive reagent, but rather the emission contacts the exposed area of the analyte-reactive reagent of the detector substrate isolated from the atmosphere and a detectable reaction occurs.

As stated above, the substrate is provided with an analyte-reactive reagent and optionally an indicator as the test field, and although it is not intended that I be bound by an explanation of the chemical reaction(s) occurring, it is believed that the analyte-reactive reagent reacts with the analyte, which results in a detectable reaction or signal (e.g., color change) in response to the reaction, thereby detecting the presence of the analyte in question. Depending on the analyte in question and the analyte-reactive reagent, the test field may include an indicator in sufficient amount to give the desired signal, e.g., color change. Further, it should be understood that the terms "analyte-reactive reagent" and "indicator" as used herein and in the appended claims can refer to either the singular or the plural depending on the choice of reagents and the chemical reactions, and therefore more than one of either reagent may be required or desirable. For example, in testing for emissions from methylisobutyl ketone, a useful analyte-reactive reagent consists essentially of potassium dichromate, sulfuric acid and water (a yellow/orange color) which, upon contact with the ketone changes to a green color. It will be observed that for such a system, no indicator is required in that the analyte-reactive reagent for the analyte in question is autogenous in that the reagent provides the color signal.

Also, it should be understood that the term "adjacent" is intended to include near, close or contiguous.

It should be understood that the substrate, per se, which is an essential member of the analytical device or detector, can be, but need not be in direct or actual contact with the component or some portion thereof. For example, in testing a flanged joint, the detector is affixed at or near one end of a plastic strip or web that is wider and longer than the detector, and, desirably, the plastic strip may be a plastic tape having at least one adhesive or tacky surface to which the detector strip is adhered. The plastic should be substantially impermeable to the analyte, substantially inert to the analyte and to the analyte-reactive reagent, and optically transparent to the detectable signal. The length of the detector strip should be sufficient to provide an adequate contact surface with the emissions and may be about equal to the outer circumference of the flange. In this manner, the detector with the plastic backing is wrapped around the flanged joint so that the detector, or a portion thereof, overlays the opening between the flanged members, and the plastic strip, being of substantially greater length, is wound upon itself so as to provide a substantially hermetic seal. Any fugitive emission from the component will contact the detector, and a detectable reaction will occur. Where desired, the detector may be of a dimension slightly longer than the outer circumference of the flange so that when wrapped around the flange, there is an overlap of detector which would be isolated from the analyte. The area of detector in the overlap region serves as a color reference or control. Also, the adhesive of the tape may not be compatible with (e.g., be reactive) the analyte-reactive reagent, and therefore a spacer member, of a plastic or other substantially inert or compatible material, is interposed between the adhesive tape and the detector. For such an embodiment, the detector and spacer member are narrower than the plastic tape.

In an alternative embodiment of the invention, the detector is disposed in a hermetic encapsulating means, such as a plastic capsule or other suitable container, which encapsulates or surrounds at least a portion of the component. The encapsulating means, e.g. capsule, should be substantially inert to the analyte, and be substantially impervious to the analyte. At least a portion of the encapsulating means is transparent so that the detector is visible. The detector may be secured or affixed to the interior surface or wall of the encapsulating means, which may be provided with an access port to allow for easy access to remove a spent or outdated detector and replace it with a new detector. The detector removed from the system may be verified for efficacy at the laboratory by treatment with the analyte in question. Where desired, the detector may be integral with the encapsulating means, as by applying or printing the necessary reagents on the interior surface or wall of the encapsulating means. Further, where desired, the encapsulating means may be provided with a bleeder valve or vent so as to permit the exhaust of gas therefrom in the event of a leak from the component. In the setup, the capsule or other suitable encapsulating means is purged with an inert gas such as nitrogen, the detector is arranged or disposed within the capsule for contact with the fugitive emission in question, and the capsule sealed to protect the detector from the ambient air or atmosphere. It may be desirable to first clean the component surface so as to minimize or avoid any false reading due to contamination, but cleaning will depend largely on the fugitive emission in question or the contamination of the component. The detector may be provided with a permeable membrane for interjacent disposition between the substrate and the component being tested, particularly if the detector, or a portion thereof, is disposed in contiguous relationship with the component, as described below in greater detail. Regardless of the particular embodiment falling within the scope of the invention, analyte as a fugitive emission being released through the component contacts the test field of the detector, which is isolated from the ambient air, and a detectable reaction occurs.

Where desired, the encapsulating means (e.g., capsule) may be provided with one or more holes or openings, or a rectangular or circular array of small holes, and the detector is then placed over the holes and secured in place as with a plastic tape. This embodiment is advantageous in that it is easy to replace a spent detector.

It will be observed that the detector, and method of using the same, requires no exogenous reagent or substance. Thus, in utilizing the detector of the present invention, no reagent external to the detector is required in preparing for or conducting the analysis as, for example, adding a reagent to the test sample to volatilize the analyte, or adding a volatile substance to the system including the test sample, or adding a diluent, or adding water or other reagent to the detector system to provide an ionized medium. As used herein and in the appended claims, exogenous reagent is intended to include not only the typical chemical reagents such as acids, bases, solvents, oxidizing or reducing agents, catalysts or inhibitors, but water as well.

Desirably the substrate comprises a material which is substantially inert to the analyte, and further is capable of holding, containing, sorbing, or otherwise being impressed with or impregnated with the reagent or reagents comprising the test field. Suitable substrate materials useful in the present invention may comprise a particulate, such as alumina, silica, glass fiber, glass beads, fritted glass, silica gel, fumed silica, carbon, or molecular sieves, which may be sorbent, and typically applied as a coating or thin layer, desirably as a planar strip, on an inert carrier or support. (Particulate as used herein and in the appended claims is intended to include powders, flakes, platelets, needles, filaments, etc., and includes both crystalline and amorphous materials.) If such particulate materials are used as the substrate, it may be desirable or necessary to adhere the particulate to a suitable carrier or support with a suitable binder which dries readily and is non-interfering with the analyte in question. Where desired, the substrate may be provided as a rigid strip or section, such as a ceramic strip of alumina or base etched glass plate, which is then coated or impregnated with an analyte-reactive reagent and, optionally, an indicator. Alternatively, the substrate may comprise papers, fabrics, foil, or films, which can be cellulosic, metallic, or synthetic, including non-wovens such as meltblown or spunbonded polyolefins, or organic polymers or copolymers such as polyethylene or nylon, or a combination thereof.

In alternative embodiments of the invention, the substrate is protected by means of an overlay for one or both surface areas. One such overlay is provided for interjacent disposition between the substrate and the component being tested, and comprises a gas-permeable membrane. That is, the membrane is permeable to the gaseous or volatile analyte, and also should be substantially inert to the analyte and to the reagent(s) applied to the substrate. This interiorly disposed overlay or membrane may be, but need not be, of substantially the same material as the substrate, and is retained in place during the test so as to protect the substrate from any contamination such as surface contamination present on or about the component.

An overlay may be provided for the oppositely disposed surface, or outwardly disposed surface of the substrate, which may be paper, film or foil. Also, this outer overlay should be substantially inert with the reagents in the substrate and with the analyte, and, depending upon the end use application, should be substantially impermeable to the gaseous analyte so as to protect the test field from analyte in the surrounding air. A particularly useful exterior overlay comprises an adhesive element or member, such as a plastic tape which is transparent to the color signal. The substrate is affixed to the tacky surface of the adhesive element and within its boundary so as to provide an overlap of the tacky surface for adherence to the component or to the encapsulating means, if desired, and in this manner, the substrate is thereby maintained in position and protected from contamination. Alternatively, both surfaces of the exterior overlay can be tacky, so that the substrate can be affixed to one surface and the whole structure be contained within the interior of the capsule, such as affixing the structure to the interior wall of the capsule, or the structure be bonded to the exterior surface over a hole in the wall of the capsule. Where, for example, the detector is designed for mounting in a capsule or on interior wall thereof, the detector is sandwiched between a permeable membrane of greater dimensions than the detector and an adhesive tape of greater dimensions than the permeable membrane to provide for an exposed tacky facing which then can be affixed or bonded to the capsule wall. In this manner, the substrate is exposed to any emission from the component undergoing a test, but is protected from the atmosphere or ambient air. Similarly, an exterior overlay such as an adhesive element is useful in mounting the detector on the exterior wall of a capsule and over one or more holes in the capsule. The adhesive element may be provided with a quick-release member, which is substantially impermeable to the analyte and protective of the detector, and is removed by the operator at the time of testing.

In still another embodiment of the invention, the detector comprises a substrate such as fumed silica, silica gel, alumina, etc., encapsulated or sandwiched between an analyte-permeable membrane and an impermeable overlay. Accordingly, the substrate bearing the analyte-reactive component is retained or supported by the membrane and overlay, which are sealed along the marginal edges, and the resulting detector element is then disposed in testing relationship with the component.

In conducting a test, the analytical device, for detecting in situ the fugitive emission, is placed adjacent the component from or through which the analyte is being emitted, and in such a manner that the substrate (and intervening membrane, if used) of the device will be contacted by the analyte. The detector, for example, may be disposed or arranged in a hermetic capsule, or disposed on the interior or exterior wall of the capsule, which had been flushed with nitrogen or other inert gas, so as to protect the detector from ambient air containing analyte which could result in a false reading. Also, where desired, the detector is provided with an exteriorly-disposed overlay impermeable to the gaseous analyte so as to protect the detector from any ambient analyte. This overlay may be integral with the detector, or may be applied as a separate means for covering the detector. The gaseous or volatile analyte reacts with the analyte-reactive reagent, thereby resulting in a color change selective or specific to the reaction. The particular analyte-reactive reagent and the concentration of the reagent applied to the substrate have been predetermined so that the moles of gaseous analyte per unit area of surface per unit of time establishes a pass or fail test. The color change, characteristic of the analyte emission, can be determined visually, or with an electronic reader utilizing a reflective photometer, or in regions of other relevant electromagnetic spectral ranges, e.g., ultra-violet (UV) range.

If a more quantitative test is desired or required, an alternative embodiment provides for an analytical element with a quantitative means for determining the release of emission rate. In this art, the term "emission" has been used interchangeably with other terms of similar or the same meaning, and is used herein to include leak, release, offgassing, degassing, desorbtion, outgassing, and the like. Thus, the substrate is produced with a concentration gradient of two or more regions of the analyte-reactive reagent, and if an indicator is used, then with a fixed concentration of the indicator. The analyte-reactive reagent relates to how rapidly the encapsulated volume retains analyte (moles analyte) sufficient to cause the analyte-reactive reagent to react substantially completely and cause a color change. Thus, as the encapsulated volume decreases or the gas emission severity increases, the faster the reaction of the analyte-reactive reagent; or as the encapsulated volume increases or the severity of the gas emission decreases, the less rapid the reaction of the analyte-reactive reagent. Each region of analyte-reactive reagent on the substrate is of increased concentration, and corresponds to a predetermined given mass for the analyte. The analyte-reactive reagent concentration regions desirably are separated by a nonreactive zone in order to facilitate the observation in color change. The amount of analyte emitted from the solid test surface which reacts with each of the analyte-reactive reagent regions of the gradient is substantially constant, but since the amount of analyte-reactive reagent in each of the regions increases, a visible stepwise color change is produced. If only a pass or fail test is required, the analyte-reactive reagent concentration gradient can be omitted.

An alternative embodiment provides for an analytical kit comprising the detector element and a control. Both the detector and control are made in accordance with the invention, except the analyte-reactive reagent is isolated from the analyte or omitted from the control. The detector and control are arranged in juxtaposition for disposition adjacent the component undergoing the test. A color change for the control indicates the presence of an interfering substance, a reagent degradation or other invalidation of the test.

DETAILED DESCRIPTION OF THE INVENTION

In accordance with the present invention, there is provided an analytical device or detector for detecting in situ the presence of a gaseous or volatile analyte as a fugitive emission from a component, e.g., juncture or joint as in a pipe line, containing a gaseous of volatile analyte. The analytical device is adaptable to be placed adjacent the component from which the analyte is emitted, as for example a gas leak in a pipe joint, and because detection is determined in situ, detection is specific to that component, and detection is relatively fast and simple and yet cumulative for detection of small leaks. These features are important because with my invention it is possible to monitor a component, testing that component only, and obviating the need for calibrations or controls and without interference from the ambient air or atmosphere. Because the detector of my invention is isolated from ambient air or atmosphere and is specific to the component in question, it is possible to monitor or identify quickly or continuously any component which may not meet governmental or industrial standards or may release a toxic or noxious gas above a tolerable or a permissible limit.

Adverse health effects and/or hazardous conditions are known to result from fugitive emissions, and governmental standards have established limits for permissible amounts of emissions from a component. For example, a typical petroleum refinery or petrochemical plant consists of an extensive network for transporting a wide variety of organic compounds, such aliphatic and aromatic compounds, and may have 100,000 to 500,000 components in this network. These components are monitored frequently, usually on a daily basis, for fugitive emissions (e.g., gas leaks), and in some instances the monitoring relies on visual or audible inspection only by an operator. Thus, monitoring is greatly simplified and expedited by using the detector of my invention.

The analytical device includes a substrate for holding a test field of the reagent, and is disposed adjacent a component so that fugitive emissions from the component contact the test field without first blending with the atmosphere. If a gas-permeable membrane is disposed interjacent the substrate bearing the test field and the component in question, as describe below in greater detail, the substrate is protected from contamination. The substrate may be disposed as or on a substantially planar strip or section such as sorbent particulate affixed or bonded to a carrier or support, because a planar strip is economical to manufacture, store, and transport, easy and economical to protect or seal from the ambient environment, easy to apply to the test material, and provides the adequate geometric area or region for holding a test field and for viewing or evaluating the test results. The substrate should be substantially inert or neutral to the analyte so as to avoid or inhibit any interference with the test reactions, and should not be influenced substantially by ambient conditions such as temperature or humidity. As explained below in greater detail, the substrate may be provided with an overlay so as to minimize or eliminate any interference or extraneous influence. The choice of substrate is determined largely by the analyte-reactive reagent(s), because the substrate should be substantially inert to the reagent or reagents and be capable of bearing the reagent(s). Suitable substrate materials include natural and synthetic materials, such as cellulose (e.g., wood cellulose, cotton, and rayon), polyolefins (e.g., polyethylene, and polypropylene), nylon, synthetic papers, glass fibers, glass beads, fritted glass, based etched glass plate or beads, silica gel, fused silica, carbon, ceramic-type materials such as alumina and silica, molecular sieves, zeolites, and the like. The substrate should avoid interfering substances. The substrate material may be applied as a thin coating on an inert carrier or support which preferably is transparent such as polyethylene or Mylar tape or film. (Mylar is a dupont trademark for a polymer of polyethylene terephthalate.) The substrate is of a suitable material capable of holding or containing or sorbing the reagent, such as being provided with a surface coating or impregnated coating of the reagent, which may be accomplished as by spraying, dipping, brushing, spreading, printing, etc., and then dried in air or preferably in an inert or non-interfering atmosphere such as nitrogen, and/or dried in a microwave oven or a low temperature oven of from about 25° to 90° C. Drying, in any case, may be conducted under reduced pressure, although the drying temperature can be higher depending largely on such factors as type of substrate, composition and concentration of the reagent, and drying time.

If an indicator is used, the indicator coating may be applied concurrently with the analyte-reactive reagent, or be applied in a separate and similar step. A test strip comprising the substrate with absorbed reagent can be bonded to a carrier such a mother roll of plastic tape that then can be cut into individual sections or strips, which should be of adequate length and width to provide a sufficient test field that can be easily handled and viewed by the tester. It will be observed that either side of the test strip can be the contacting side, and other side for observing the test results (unless there is an interjacent membrane, described below). Test strips or sections of this type can be easily protected from ambient condition, and stored in a sealed or hermetic container, which is substantially impermeable to the analyte such as a multilayer polymeric material (e.g., "Curpolene" manufactured by Bemis-Curwood Co., New London, Wis.) Hermetic storage can be important when the detector is to be used in an area where the surrounding air contains the analyte, as for example in a petroleum refinery.

The substrate, or at least a portion thereof, is provided with a test field comprising an analyte-reactive reagent. The reagent has been preselected for the particular analyte so that there takes place on the test field a chemical reaction between the reagent and analyte, and results in a color change of the test field. An indicator may be included in the test field in order to achieve the color change, but this depends largely upon the analyte. The analyte-reactive reagent is applied to at least a portion of the substrate typically as a solution as by dipping, spraying, spreading, brushing, or printing. Depending largely upon the type of substrate and the specific reagent, a diluent, viscosity agent, dispersing agent, surfactant, or the like, may be used in the application of the analyte-reactive component to the substrate, which is within the skill of the art or may be determined by routine experimentation, and this aspect is not part of the present invention. It should be understood that depending largely on the type of substrate and physical nature of the analyte-reactive reagent, the substrate may be coated, impregnated, sorbed, or otherwise impressed with the reagent, and as used herein and in the appended claims, the terms "applied" or "contain" when used in this context is intended to be used in the broad sense as including any one of these techniques or similar techniques for holding the reagent.

Where desired, the analyte-reactive reagent is applied to the test field of the substrate in a substantially uniform concentration, and a pass or fail test result can be determined by the operator. If a concentration gradient is desired for a more quantitative reading (as described below in detail) with a substrate having two or more test regions, then a uniform concentration of the reagent is applied to each region and the concentration varies between regions. In this manner, the color change or color signal will appear substantially uniformly over the entire test field or over each region of the test field. If an indicator is included, the analyte-reactive reagent selected is chemically compatible with the indicator so as to result in a color change or signal, which preferably can be determined visually or by other means such as UV light. For example, in detecting for fugitive emissions of a volatile organic compound from a component, e.g. juncture, in a petroleum refinery, a suitable analyte-reactive reagent consisting essentially of chromium compounds with the chromium having a +6 valence and sulfuric acid will detect, for example, ketones, low molecular weight hydrocarbons (e.g., $C_3$ or $C_4$), petroleum distillates, gasoline and vinyl chloride; and these reagents are useful with such substrate materials as silica gel or ceramics, are soluble in water, and can be easily applied to the substrate as an aqueous solution and dried at a relatively low or moderate temperature. Many of these chromium containing reagents have an orange or yellow color and yield a green color or green/brown color or brown color, which provides for easy detection. If one is interested in testing for $C_5$ and above, for benzene, or for xylene emissions, a suitable analyte-reactive component comprises iodine pentoxide and sulfuric acid exhibiting a white color any yielding a brown/black color. The particular color signal is preselected, and preferably is in the visual range, but may be in the UV range.

It may be desirable or necessary to incorporate an indicator into the test field of the substrate to provide a color signal, and the choice depends largely on the analyte and analyte-reactive reagent. The indicator typically is applied to the substrate as a solution, which may be either aqueous or organic, depending on the composition of the indicator. The analyte-reactive reagent may be applied first to the substrate, and after adequate drying, the indicator is then applied, although it some instances it may be desirable to apply both materials at the same time. Here, too, the particular method of application of indicator to the substrate can be by any conventional or known means, such as by dipping, brushing, spreading, spraying, or printing, and then dried in an analyte-free or non-interfering atmosphere, e.g., nitrogen, and may be dried at an elevated temperature as in an oven, essentially as described with reference to the analyte-reactive reagent. Generally, the indicator is applied to the substrate or test field in a manner which produces a "lawn" of uniform fixed concentration. In this manner, a substantially uniform color signal will occur over an entire test region of the substrate.

An indicator is useful in detecting for gaseous emissions of formaldehyde, as described in my copending application U.S. Ser. No. 07/814,720, and incorporated herein by reference. Thus, a planar strip as the substrate (e.g., a paper or synthetic strip) is impregnated with an analyte-reactive reagent such as hydroxylamine phosphate and with an indicator such as Bromophenol Blue. The indicator, which originally is purple/blue, will change to yellow after exposure to formaldehyde.

If the substrate is provided with a concentration gradient, then the region of the gradient with the lowest concentration of analyte-reactive reagent changes color first, and those regions of higher concentration change color more slowly, with the region of highest concentration changing to color last. Thus, detectors prepared with lower concentrations of analyte-reactive reagent are more sensitive to the analyte, in that the color changes are detected at lower emission rates due to the lower concentration.

In a preferred embodiment of the invention, a membrane is provided for interjacent disposition between the substrate and the source of the fugitive emission, e. g. a gas leak in a joint or juncture. The membrane is permeable to the gaseous or volatile analyte, and also is substantially inert to, or neutral with the analyte. For this particular embodiment, the gaseous or volatile analyte in the test zone permeates the membrane and then contacts the test field of the substrate. It is advantageous to employ a membrane in order to protect the substrate from contamination during storage and, most significantly, from nonvolatile contaminants that may be present on the component being tested. It therefore is desirable to provide a membrane which is of essentially the same dimensions or of slightly larger dimensions than the geometric area occupied by the substrate. If the membrane is of larger dimensions than the substrate area, information such as a printed calibration scale visible to the operator can be provided along one or both sides of the membrane which, when calibrated to a standard, shows the concentration gradient of analyte emitted. Also, if the dimensions of the membrane are greater than that of the substrate, the overlapping portion of the membrane can provide a section for handling by the operator without touching the test field of the substrate and as a reference. In an alternative embodiment, the detector is provided with an exteriorly disposed overlay having a tacky surface or facing, which is described below in greater detail, and therefore the substrate and membrane can be bonded or affixed to the tacky surface of the overlay. Any of a number of materials may be used for the permeable membrane structure, including natural and synthetic materials, such as Teflon (a tetrafluoroethylene resin manufactured by DuPont), polyolefin nonwovens, nylon, glass fiber, fritted glass, paper, cotton, rayon, etc. The substrate and membrane may be comprised of essentially the same material or of different materials. It should be understood that the term "permeable membrane" as used herein and in the appended claims is intended to include a semipermeable membrane.

In an alternative embodiment, there is provided an overlay of paper, film, or foil, or a combination thereof, for the oppositely disposed surface, or outwardly disposed surface, of the substrate. Suitable overlay materials include, for example, paper impregnated with a plastic to be substantially impermeable, rigid and semirigid polymers and/or copolymers such as Mylar, polycarbonates, polyolefins, silica glass, Saran (a trademark of Dow Chemical Co. for a polymer of vinylidene chloride), and metal foil. This outwardly disposed overlay should be substantially inert to the reagents in the substrate and with the analyte, and further should be substantially impermeable to the gaseous analyte. In accordance with one embodiment, the outwardly disposed overlay serves as a carrier for the substrate, and comprises an adhesive element or member, for example clear polyethylene tape, and may be of sufficient dimensions so as to extend beyond the marginal edges of the substrate. In such a case, the substrate is affixed or bonded to the tacky surface of the adhesive element and within its boundary so as to provide an overlap of the tacky surface for adherence to the members of the test component (e.g., flanged fittings in a joint) or to the interior wall of the capsule surrounding the component. Alternatively, a spacer, which is substantially inert to the analyte and the analyte-reactive reagent and is transparent to the color signal, may be interposed between the adhesive element and the detector substrate. A spacer, desirably of a plastic, is useful if the reagent reacts with the carrier or the adhesive of the carrier. If a permeable membrane is used in the detector, as described above, it is desirable that the dimensions of the membrane be greater than that of the substrate but less than that of the outer overlay, and in that manner both the substrate and membrane can be affixed or bonded to the adhesive overlay, thereby forming a composite encapsulating the substrate and protecting it from contamination. The adhesive element should be substantially impermeable to the analyte, substantially inert to the analyte-reactive component, and optically transparent to the color signal. Particularly suitable materials are, for example, clear polyethylene and Mylar as tape or film. When the adhesive element bearing the substrate is applied to the test zone, the substrate is thereby maintained in position and protected from contamination for the duration of the test. It is desirable to provide the tacky surface of the adhesive element with a quick-release member, which can be removed by the operator at the time the detector is to be utilized for the test. Where desired, the surface adhesivity of the carrier may be enhanced by corona treatment, flame treatment, or irradiation. Alternatively, the surface of the plastic carrier may be heat softened so as that the substrate can be pressed into the soft surface, and upon cooling becomes fastened or affixed in place.

Figure 1:
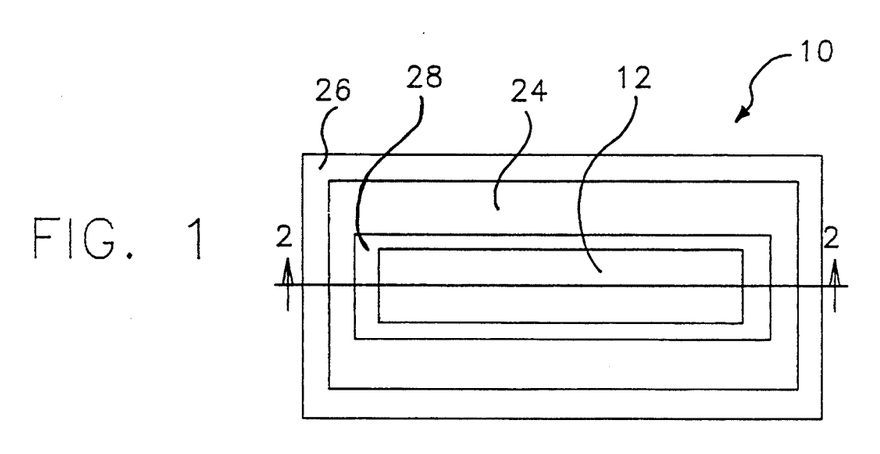
FIG. 1 is a plan view illustrating a one embodiment of the detector of the present invention.
Figure 2:
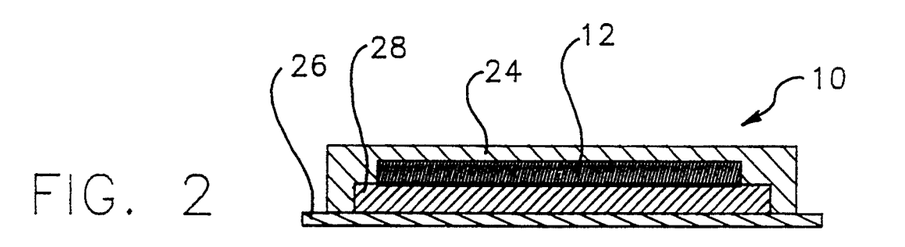
FIG. 2 is a side elevational view in cross section of the detector shown in FIG. 1 and shown on line 2—2 of FIG. 1, with dimensions exaggerated for purposes of clarity.
Figure 3:
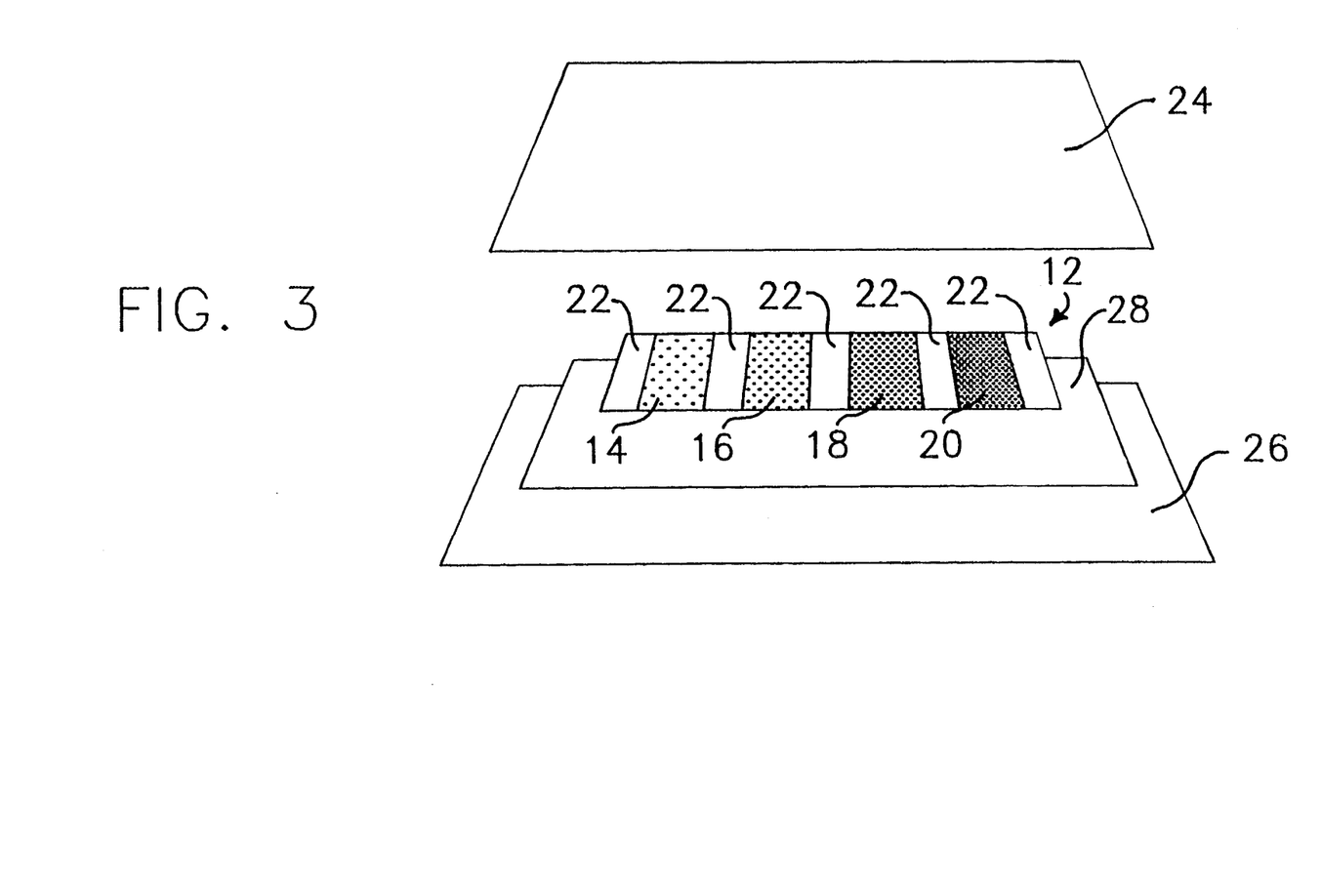
FIG. 3 is an exploded perspective of the analytical device of FIG. 1.

FIGS. 1, 2 and 3 illustrate one embodiment of the invention. In the drawings, wherein like reference numerals refer to similar parts throughout the views, there is shown an analytical device or detector indicated generally by the numeral 10. The device comprises a substrate or test strip 12, which may comprise, for example, a Mylar film having applied thereto a sorbent such as silica gel or fused silica as the substrate impregnated with an analyte-reactive reagent. The substrate of the test strip may be provided with a concentration gradient in order to provide for a quantitative reading, as illustrated in FIG. 3, and includes four regions 14, 16, 18 and 20, but more or less regions can be provided depending upon the particular need. Each region is provided with a known concentration of analyte-reactive reagent, with region 14 having the lowest concentration and region 20 having the highest concentration. If an indicator is used, there is a fixed lawn of indicator throughout the test strip, and each test region is separated by an area 22 having indicator only. One surface of the detector (the exterior surface when in test position) is provided with an overlay 24 comprising, for example, a clear or transparent polyethylene tape, and the test strip is adhered to the tacky surface of the tape. A quick release member 26 is provided for the back surface or tacky surface of the overlay 24 to protect it until ready for use, at which time the release member is removed and the detector disposed adjacent the test component. In an alternative embodiment, the opposite surface of the test strip with substrate is provided with a gas permeable membrane 28, such as Teflon, for interjacent disposition between the test substrate and the component. As shown, the membrane overlaps the substrate, and therefore those surfaces of the membrane extending beyond the substrate are adhered to the tacky surface of the tape overlay. In this manner, the substrate is maintained in a secure position and is kept free of contamination. Where desired, a printed calibration scale may be provided along one side of the test strip 12, and this calibration scale may be printed onto the membrane or the overlay, or be provided as a separate strip and affixed to the overlay. In order to protect the detector from the surrounding air, the detector may be hermetically bagged for storage.

The analytical device such as of the structure shown in the drawings can be readily utilized at the test site and without the need for additional or special instrumentation. In use, the release member or backing 26 is removed, and the detector is promptly placed in the test zone of the component such as mounted in a capsule surrounding the component. With this particular embodiment, the substrate 12 is protected by the membrane 28 from any contamination that may be present, and by the tape 24 from any analyte present in the ambient air. As shown in FIG. 3, for example, test region 14 would have a concentration of reagent that upon reaction with the analyte would give a color signal slightly below the permissible limit; region 16 would have a concentration of reagent that would give a color signal at the permissible limit; region 18 would give a color signal slightly above the limitation; and region 20 would give a color signal substantially above the limitation. Thus, from the timed interval to the color signals, the test operator would not only know if the material passed or failed, but also have a quantitative indication.

Figure 4:
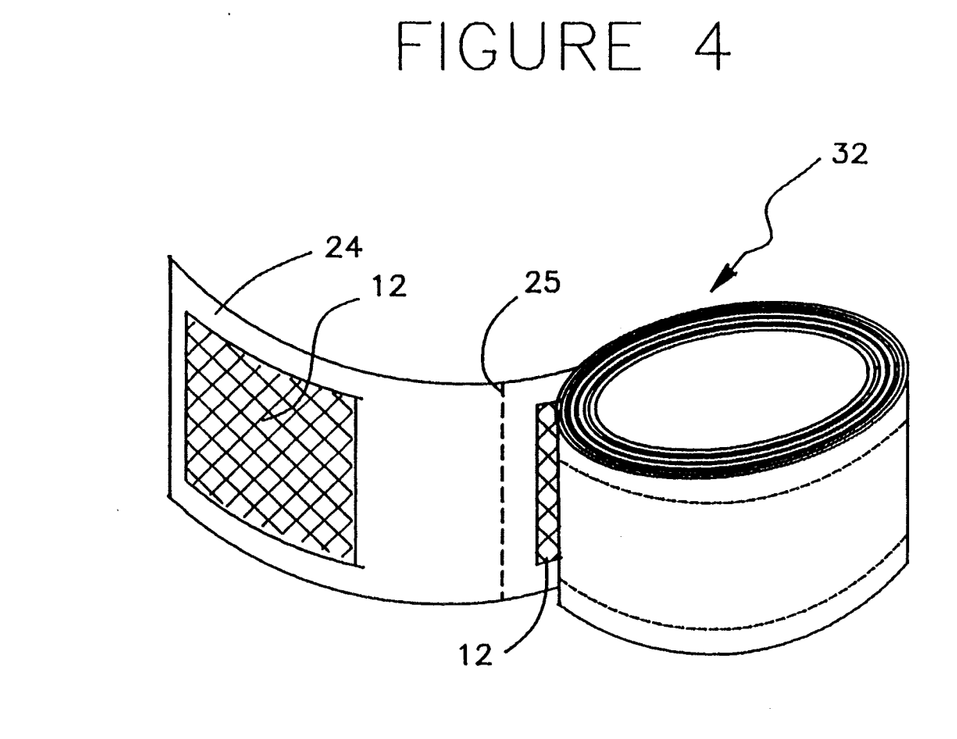
FIG. 4 is a perspective view showing an alternative embodiment of the analytical device of the present invention.
Figure 5:
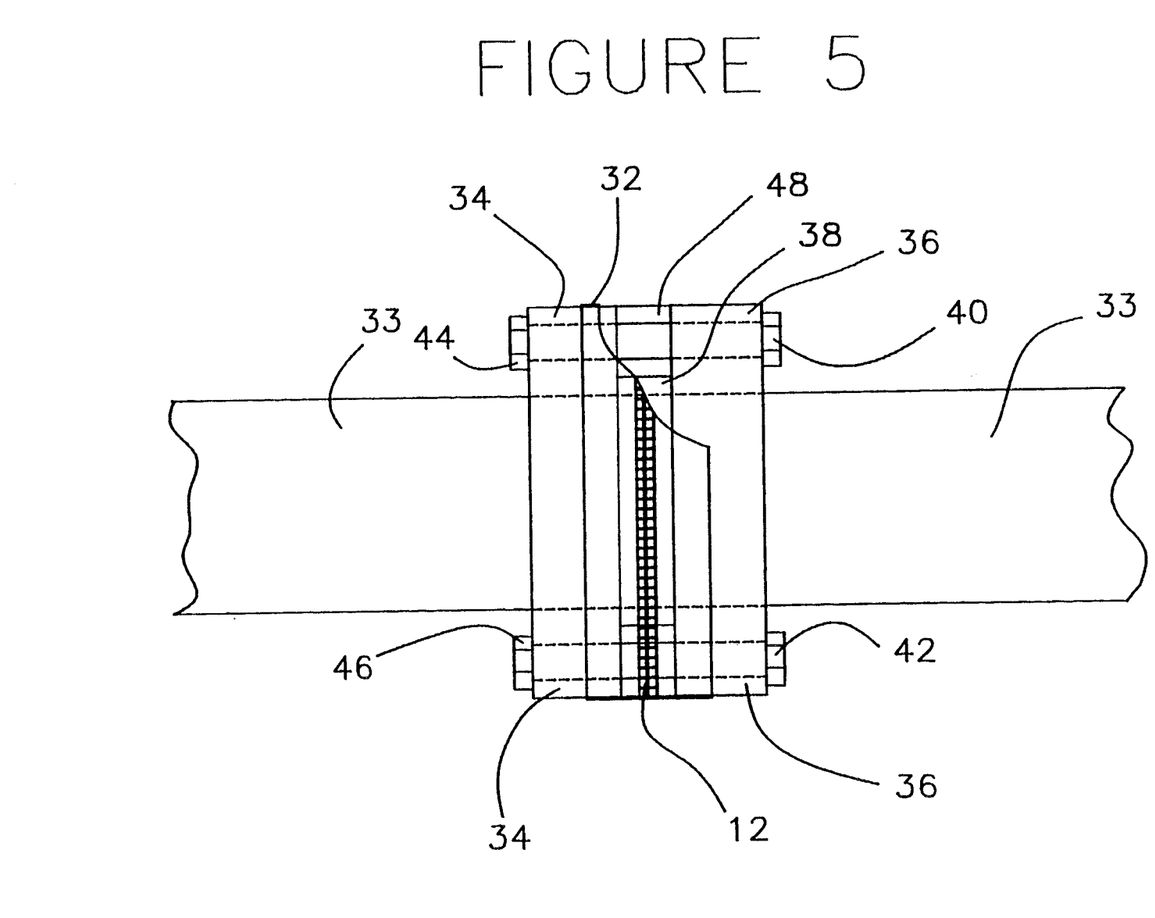
FIG. 5 is a side elevational view of the embodiment of FIG. 4 shown in position at a flanged juncture.

In accordance with the embodiment shown in FIG. 4, the analytical device is provided in a substantially continuous form such as a roll, indicated generally by the numeral 32, comprising test strip 12 disposed in intermittent lengths on an adhesive overlay 24. The test strip should have sufficient dimensions to span a section of the component and to provide a meaningful test field. Although the test strip shown in all the figures is -rectangular, any shape or dimension may be used, the detector may be a packet or pouch, and the ratio of detector to tape will depend largely upon the component being tested. It will be observed that the test strip is adhered to the tacky surface or facing of the overlay. Because the test strip is narrower than the overlay, when wound into a rolled form, typically on a paper or plastic core (not shown), the tacky facing of the overlay adheres to the opposed nontacky facing. In this manner, the detector is self-sealing and thereby protected from analyte in the surrounding air. Although the overlay tape 24 is of substantially continuous length, the detector strip 12 may be discontinuous, having a relatively short length, and these short strips are spaced apart from one another on the overlay backing at selected intervals or distances as required to define an individual detector of meaningful size for the particular test operation. Also, a membrane may be provided for intermediate disposition between the test strip and the component from which a fugitive gas is emitted. When required by the test operator, a detector may be dispensed from the roll, and a desired length is then cut from the roll. If desired, the overlay 24 may be provided with intermittent score lines 25 in order to facilitate severing the detector from the roll. This embodiment would be particularly useful for testing a flanged joint for pipe line 33 having flange members 34 and 36, with interposed gasket 38, connected by threaded bolts 40 and 42 for engagement with nuts 44 and 46, as shown in FIG. 5. The tape 32 is positioned onto the adjacent flange members 34 and 36 so that the test strip 12 is exposed to the gap 48 between the flanges and thereby will be contacted by any fugitive emissions, and the tape wound or overlapped upon itself for a sufficient length so as to provide a hermetic seal. As explained above, the detector strip may be of a length about equal to the circumference of the flange members, or may be slightly longer so as to provide an overlap whereby the overlap serves as a reference.

In still another embodiment of the invention, a detector kit is provided in order to determine the validation/invalidation of the test for the desired analyte. For the kit, a second substrate is prepared in essentially the same manner as the above described substrate with a test field. The two substrates are placed adjacent each, such as being affixed in juxtaposition to the tacky facing of an adhesive overlay (described above) which is then disposed adjacent the test component, and the second substrate is further encapsulated or sealed from contact with the analyte. The two substrates are examined at the same time to determine if any interfering substances were present. In the event the test for the analyte is valid in that an analyte is emitted from a leak in a component, the first substrate with an analyte-reactive reagent will render a color signal, while the control strip will not. In the case of an invalid test for the analyte in question, both substrates will change color.

Figure 6:
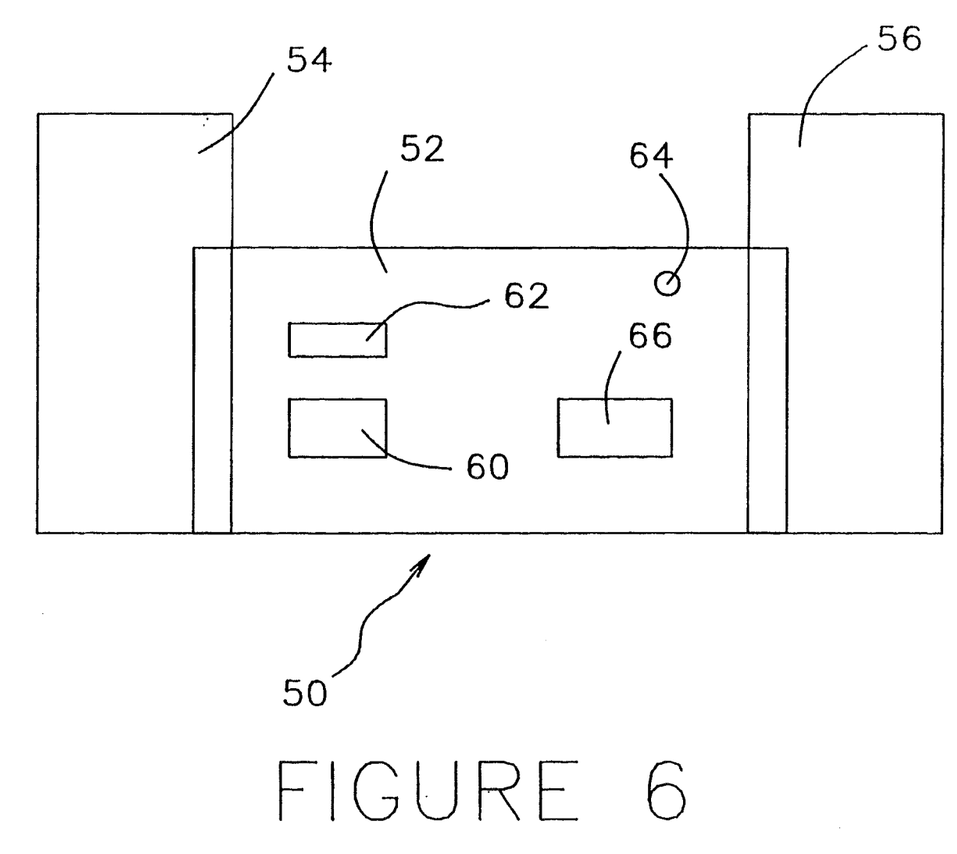
FIG. 6 is a plan view illustrating an alternative embodiment of the invention shown as a flat pattern before being emplaced and suitable for encapsulating a component such as a flanged juncture.
Figure 7:
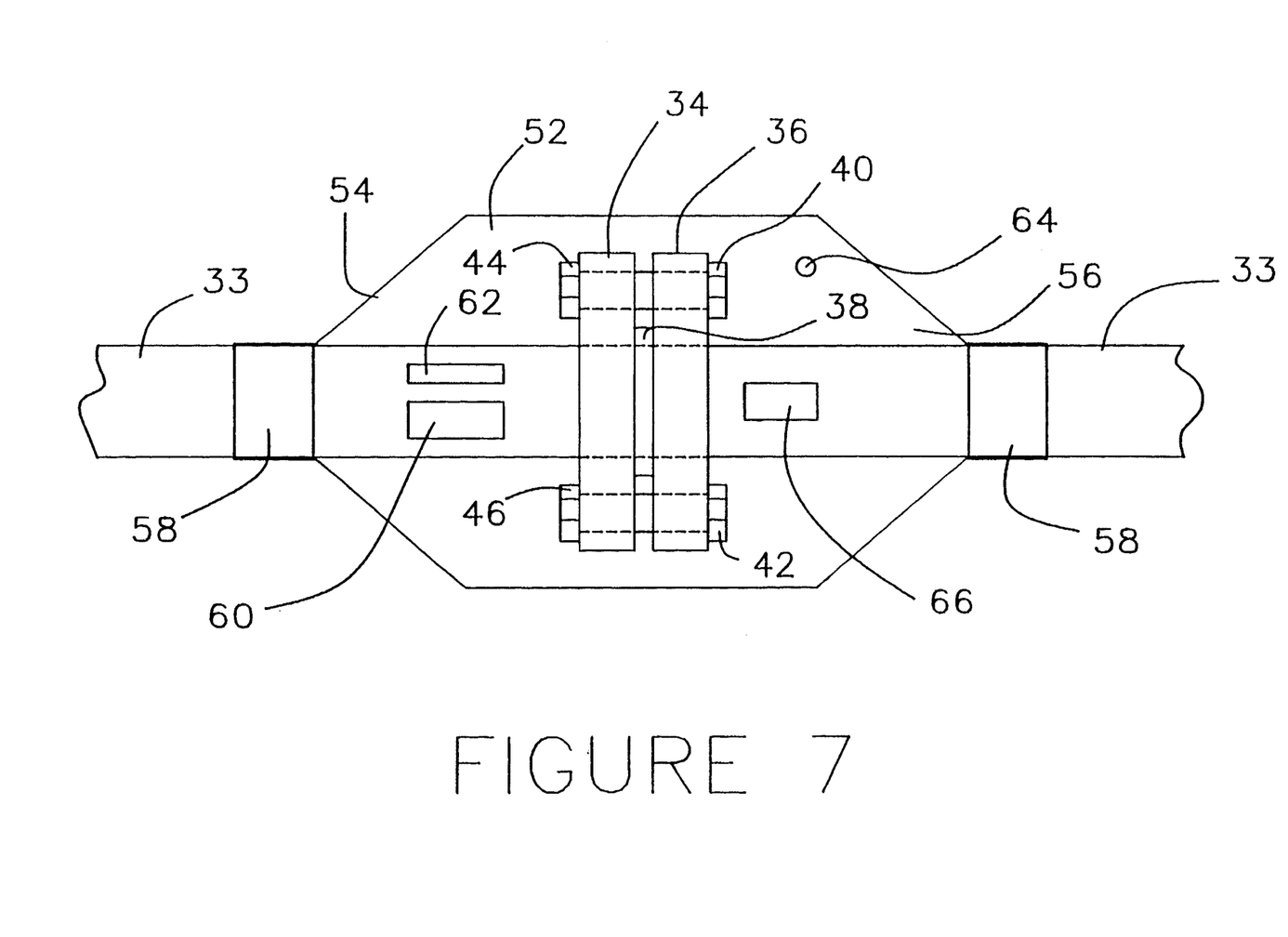
FIG. 7 is a side elevational view of the embodiment of FIG. 6 shown in position at a juncture.

In accordance with the embodiment shown in FIGS. 6 and 7, the detector system includes and encapsulating means, indicated generally by the numeral 50, for encapsulating the test component, e.g., a joint. Capsule 50 includes a central section 52 and opposed ends 54 and 56. The central section is formed of a plastic film, e.g., Mylar, and of sufficient thickness and rigidity so as to permit handling and wrapping about a component such as a pipe joint, and as shown in FIG. 7, the central section is formed about the component so as to be of a substantially cylindrical configuration. The opposed ends 54 and 56 are formed of a relatively more flexible plastic, either formed integrally with the central cylindrical section or formed of a different material and sealed to the central section, so as to be wrapped tightly about the circumference of a pipe and be sealed by means of tape 58. The central body or cylinder 52 includes an access port 60 to provide easy access to the interior of the capsule for positioning and replacing detector strip 62. A bleeder valve or vent 64 is provided to allow for the exhaust of any excess gases. Also, a bar code or other identifier 66 may be positioned on the capsule for computer reading of data such as the date and time of checking the joint. Thus, it will be observed from FIG. 7 that the capsule 50 encapsulates the flanged members 34 and 36 by arranging the cylindrical section 52 about the flanged members, but preferably not in contact with them, and the overlapping ends 54 and 56 are tightly sealed to the pipe line 33 as with tape 58. Any fugitive emission from the juncture leaks into the capsule and reacts with the detector, which can be visible observed by the operator.

Figure 8:
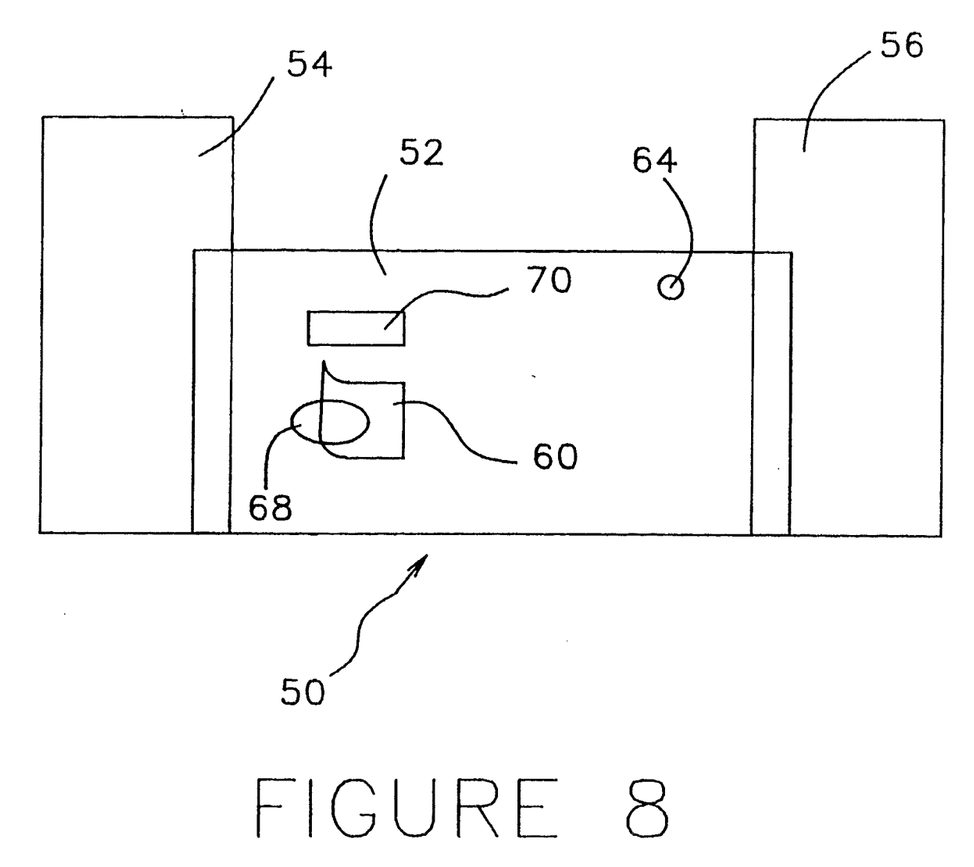
FIG. 8 is a plan view showing a modification of the device of FIG. 6.

A modified form of the capsule 50 is shown if FIG. 8. In accordance with this embodiment, the detector is disposed on the exterior surface or wall of the capsule. The wall of the central section 52 is provided with at least one opening 68, and the detector 60 is disposed over the hole. The detector substrate may be affixed to the tacky surface or facing of a clear tape but within the marginal edges thereof, and the tape then bonded to the wall of the cylindrical section 52. The tape completely covers the hole, and therefore any emission from a leak in the component will contact the detector. Instead of one hole in the capsule wall, the wall may be provided with a plurality of smaller holes. Also, a control 70 may be disposed on the exterior surface of the central section 52, and covered with an impermeable tape. If the control changes color, the test then appears to be invalid.

Tile invention is further illustrated by the following examples.

EXAMPLE I

A detector was prepared by sorbing a small volume of an analyte-reactive reagent consisting of 0.5 g $Na_2Cr_2O_7$ + 0.5 mL $H_2O$ + 9.5 mL of $H_2SO_4$ onto 1 g silica gel (Fisher Scientific Company, Fair Lawn, N.J.). The silica gel with sorbent was then heated/dried for several seconds in a microwave oven. The resulting substrate was yellow to orange in color depending upon the volume of solution sorbed by the silica gel. The substrate changed color upon exposure to the following gaseous or volatile analytes:

| Analyte | Color Change |
| --- | --- |
| methylisobutylketone | yellow/orange to green |
| propane | yellow/orange to green |
| butane | yellow/orange to green |
| petroleum distillates | yellow/orange to green/brown |
| gasoline | yellow/orange to brown |
| mixture (methylethylketone, tetrahydrofuran, cyclohexanone polyvinyl chloride) | yellow/orange to light green |

EXAMPLE II

A substrate was prepared as in Example I, except that the $Na_2Cr_2O_7$ was replaced by $K_2Cr_2O_7$. The tests results for the same analytes were similar to those shown in the table for Example I.

EXAMPLE III

Substrates were prepared as in Example I but using other forms of silica, as follows: fumed silica (Sigma Chemical Company, St. Louis, Mo.), silica gel beads (EM Science Industries, Cherry Hill, N.J.), and chromatography grade silica (Fisher Scientific Company). The color changes observed for the same analytes as those of Example I were similar as those shown in the table.

EXAMPLE IV

Substrates were formed as described in Examples I, II, and III, except that the solutions were diluted prior to sorption with distilled deionized water to 25% and 10% of the initial reagent solution concentration. In all cases, the nascent substrates were yellow. Increases in the rates at which the color changed and decreases in color intensity of the analyte exposed substrates were observed.

EXAMPLE V

Substrates taken from Examples I, II, and IV were individually exposed to the following liquid analytes: methylisobutylketone, gasoline, petroleum distillates, and mixture from the table in Example I. The observed color changes were as with the gaseous analytes described above.

EXAMPLE VI

Substrates were prepared by sorbing directly the solutions used in Examples I and II directly on fritted glass filters (Pyrex, Corning, Inc., N.Y.). Color changes were as describe above when those filters were exposed to gaseous analytes described in the Lable of Example I; however, increases in the rate at which the observed color changed were apparent.

EXAMPLE VII

The tests described in Example I and II were performed with substrates immobilized on: Mylar semirigid films, polystyrene, polyethylene tape (#CW-1, Manco, Inc., West Lake, Ohio), Plexiglass, and glass plates (VWR Scientific Company, San Francisco, Calif.). Results were essentially the same as those described in the table of Example I.

EXAMPLE VIII

Tests were made as described in Examples V and VII, except that a semipermeable membrane was placed between the analyte sources and the substrates. The semipermeable membrane materials used were: fritted glass (Corning, Inc.), filter paper (Whatman, Co., Hillsboro, Oreg.), and Teflon film. The results were essentially the same as those described in the referenced examples.

Having described my invention, and certain embodiments thereof, I claim:

1. A source specific detector for detecting a fugitive emission from a component containing a gaseous or volatile analyte, comprising a substrate adaptable for disposition adjacent said component, means for isolating said substrate from ambient atmosphere, said substrate having applied thereto an analyte-reactive reagent which reacts with said analyte producing a detectable signal selective to the reaction thereby detecting said analyte as a fugitive emission; and said detector requiring no exogenous reagent.

2. A detector according to claim 1 wherein said substrate is an inorganic material capable of sorbing said analyte-reactive reagent.

3. A detector according to claim 1 or claim 2 wherein said substrate is an inorganic particulate.

4. A detector according to claim 3 wherein said substrate is selected from the group consisting of glass fiber, glass beads, fritted glass, ceramic, silica, silica gel, fumed silica, carbon, or molecular sieves.

5. A detector according to claim 3 wherein said substrate is disposed on a substantially inert carrier. detectable signal.

6. A detector according to claim 5 wherein said carrier is a planar strip.

7. A detector according to claim 6 wherein said carrier is a material selected from the group consisting of paper, fabric, nonwovens, plastic film, or foil.

8. A detector according to claim 1 wherein said substrate having applied thereto an indicator in sufficient amount to produce said 9. A detector according to claim 1 including a membrane applied to said substrate for interjacent disposition between said substrate and said component, said membrane being permeable to said analyte and substantially inert to said analyte and said analyte-reactive reagent.

10. A detector according to claim 9 wherein said membrane is a permeable plastic film.

11. A detector device according to any one of claim 1, 2 or 8 wherein said isolating means comprises an overlay for said substrate, said overlay being substantially impermeable to said analyte, being substantially inert to said analyte and to said analyte-reactive reagent, and optically transparent to said detectable signal.

12. A detector according to claim 11 wherein said overlay has a tacky facing.

13. A detector according to claim 12 including a release member overlaying said tacky facing.

14. An detector according to claim 11 including a spacer member interposed between said overlay and said substrate, said spacer member being substantially inert to said analyte-reactive reagent and optically transparent to said detectable signal.

15. A detector according to claim 11 wherein said overlay is polyethylene.

16. A detector according to claim 11 wherein said overlay is Mylar.

17. A detector according to claim 11 which includes said substrate having a concentration gradient of said analyte-reactive component defining a plurality of concentration regions.

18. A detector according to claim 17 wherein each concentration region is separated by one or more nonreactive zones.

19. A detector according to claim 1 or claim 2 including a membrane applied to said substrate for interjacent disposition between said substrate and said component, said membrane being permeable to said analyte and substantially inert to said analyte and said analyte-reactive reagent, and said isolating means comprises an overlay for said substrate, said overlay being substantially impermeable to said analyte, being substantially inert to said analyte and to said analyte-reactive component, and optically transparent to said detectable signal.

20. A detector according to any one of claims 1 or 2 wherein said isolating means comprises a hermetic encapsulating means for enclosing said detected and adaptable to encapsulate at least a portion of said component.

21. A detector according to claim 20 wherein said encapsulating means comprises a capsule substantially encapsulating said component, said capsule having at least a transparent section, and a bleeder valve for emitting gas to the atmosphere.

22. A detector according to claim 21 wherein said capsule comprises a plastic.

23. A detector according to claim 22 further including a membrane applied to said substrate for interjacent disposition between said substrate and said component, said membrane being permeable to said analyte and substantially inert to said analyte and said analyte-reactive reagent.

24. A detector according to claim 23 further including an adhesive element having a tacky facing overlaying said substrate on the surface opposed to said membrane.

25. A detector according to claim 24 wherein said tacky facing is bonded to the interior of said capsule.

26. A detector according to claim 24 wherein said capsule has an opening, and said tacky facing is bonded to the exterior of said capsule over said opening.

27. A detector according to claim 22 wherein said analyte-reactive reagent is applied directly to the interior surface of said capsule.

28. A detector according to claim 22 wherein said analyte-reactive reagent and said indicator are applied directly to the interior surface of said capsule.

29. A detector according to claim 20 wherein said detector is mounted interiorly in said encapsulating means.

30. A method for detecting the presence of a fugitive emission from a component containing a gaseous or volatile analyte, which comprises providing a substrate having an analyte-reactive reagent which reacts with said analyte in sufficient quantity to produce a color specific to the reaction thereby detecting the presence of said analyte, placing said substrate adjacent said component, isolating said substrate from ambient air, allowing sufficient time for said reaction to occur, and observing any change in color on said substrate.

31. A method according to claim 30 and further including providing an overlay for said substrate, said overlay being substantially impermeable to said analyte.

32. A method according to claim 31 and further including a membrane applied to said substrate for interjacent disposition between said substrate and said component, said membrane being permeable to said analyte and substantially inert to said analyte and said analyte-reactive reagent.

33. A method according to claim 32 wherein said substrate is an inorganic particulate.

* * * * *